United States Patent
Branch et al.

(10) Patent No.: US 10,130,609 B2
(45) Date of Patent: Nov. 20, 2018

(54) PYRAZOLE DERIVATIVES AND THEIR USES THEREOF

(71) Applicants: CANADIAN BLOOD SERVICES, Ottawa (CA); UNIVERSITY HEALTH NETWORK, Toronto (CA)

(72) Inventors: Donald R. Branch, Toronto (CA); Lakshmi P. Kotra, Toronto (CA)

(73) Assignees: UNIVERSITY HEALTH NETWORK, Toronto (CA); CANADIAN BLOOD SERVICES, Ottawa (CA)

(*) Notice: Subject to any disclaimer, the term of this patent is extended or adjusted under 35 U.S.C. 154(b) by 32 days.

(21) Appl. No.: 14/775,449

(22) PCT Filed: Mar. 12, 2014

(86) PCT No.: PCT/CA2014/050222
§ 371 (c)(1),
(2) Date: Sep. 11, 2015

(87) PCT Pub. No.: WO2014/138979
PCT Pub. Date: Sep. 18, 2014

(65) Prior Publication Data
US 2016/0022640 A1 Jan. 28, 2016

Related U.S. Application Data

(60) Provisional application No. 61/778,884, filed on Mar. 13, 2013, provisional application No. 61/778,865, filed on Mar. 13, 2013.

(51) Int. Cl.
| | | |
|---|---|---|
| *C07D 231/12* | (2006.01) | |
| *C07D 403/12* | (2006.01) | |
| *C07D 403/06* | (2006.01) | |
| *C07D 231/22* | (2006.01) | |
| *C07D 231/46* | (2006.01) | |
| *C07D 231/20* | (2006.01) | |
| *A61K 31/4155* | (2006.01) | |
| *A61K 45/06* | (2006.01) | |

(52) U.S. Cl.
CPC .......... *A61K 31/4155* (2013.01); *A61K 45/06* (2013.01); *C07D 231/12* (2013.01); *C07D 231/20* (2013.01); *C07D 231/22* (2013.01); *C07D 231/46* (2013.01); *C07D 403/06* (2013.01); *C07D 403/12* (2013.01)

(58) Field of Classification Search
CPC .. C07D 231/20; C07D 231/22; C07D 231/46; C07D 403/06; C07D 403/12; C07D 231/12
See application file for complete search history.

(56) References Cited

U.S. PATENT DOCUMENTS

| | | | |
|---|---|---|---|
| 4,171,367 A | 10/1979 | Winn et al. | 514/392 |
| 5,006,520 A | 4/1991 | Oe et al. | 514/217.07 |
| 8,063,058 B2 | 11/2011 | Jia et al. | 514/275 |
| 8,138,339 B2 | 3/2012 | Bauer et al. | 544/297 |
| 8,158,621 B2 | 4/2012 | Singh et al. | 514/229.5 |
| 8,227,472 B2 | 7/2012 | Caruso et al. | 514/254.06 |
| 2008/0051418 A1* | 2/2008 | Maekawa | C07D 213/30 514/256 |
| 2009/0028871 A1 | 1/2009 | Kim et al. | 424/145.1 |
| 2009/0298823 A1 | 12/2009 | Song et al. | 514/234.2 |
| 2010/0047249 A1 | 2/2010 | Branch | 424/141.1 |
| 2010/0093698 A1 | 4/2010 | Bahmanyar et al. | 514/210.21 |
| 2010/0190749 A1 | 7/2010 | Ren et al. | 514/64 |
| 2011/0104186 A1 | 5/2011 | Valiante et al. | 424/184.1 |
| 2011/0251177 A1 | 10/2011 | Yu et al. | 514/211.15 |
| 2012/0101275 A1 | 4/2012 | Jia et al. | 544/324 |

(Continued)

FOREIGN PATENT DOCUMENTS

| | | |
|---|---|---|
| EP | 2033955 | 3/2009 |
| WO | WO 2002/009662 | 2/2002 |

(Continued)

OTHER PUBLICATIONS

Hassan et al. "Phase Transfer Catalyzed C- vs O-Alkylation of 3-Methyl-1-phenyl-2-pyrazolin-5-one in the Absence of Presence of Carbon Disulphide" Heterocycles 1997, 45, 451-465.*

(Continued)

Primary Examiner — Amanda L Aguirre
(74) Attorney, Agent, or Firm — Norton Rose Fulbright US LLLP (57) ABSTRACT

The present disclosure relates to a compound of formula (I) or a pharmaceutically acceptable salt thereof; wherein U, R1, R2, R3 and Q are as defined herein. The disclosure also provides a method for treating or preventing a method for the prevention, treatment and/or alleviation of one or more autoimmune or alloimmune disease, pharmaceutical compositions and combination comprising a therapeutically effective amount of a compound, as defined herein.

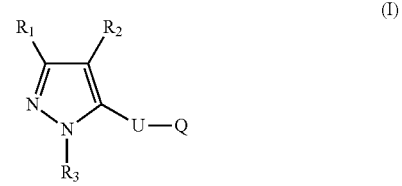

13 Claims, 2 Drawing Sheets

(56) References Cited

U.S. PATENT DOCUMENTS

| | | | | |
|---|---|---|---|---|
| 2012/0129867 A1 | 5/2012 | Bauer et al. | ............. | 514/252.14 |
| 2012/0130073 A1 | 5/2012 | Jia et al. | ....................... | 544/296 |

FOREIGN PATENT DOCUMENTS

| | | |
|---|---|---|
| WO | WO 2011/042798 | 4/2011 |
| WO | WO 2011/092140 | 8/2011 |

OTHER PUBLICATIONS

Fruchier et al. Can. J. Chem. 1985, 63, 375-80. (Year: 1985).*
Database Registry [Online] Chemical Abstracts Service, Columbus, Ohio, US; Feb. 27, 2012 (Feb. 27, 2012), "1H-Pyrazole, 1-methyl-5-[[1-methyl-3-(1,1,2,2,2-pentafluoroethyl)-1H-pyrazol-5-yl]oxy]-3-(1,1,2,2,2-pentafluoroethyl)-4-(trifluoromethyl)-",XP002751493, Database accession No. 1357625-31-0.
Database Registry [Online] Chemical Abstracts Service, Columbus, Ohio, US; Nov. 2, 2011 (Nov. 2, 2011), "1H-Pyrazole-4,5-diamine, 1,3-dimethyl-N5-[(1-methyl-1Hpyrazol-5-yl)methyl]-", XP002751494, Database accession No. 1339733-80-0.
Database Registry [Online] Chemical Abstracts Service, Columbus, Ohio, US; Apr. 24, 2011 (Apr. 24, 2011), "1H-Pyrazol-4-amine, 1,3-di methyl-5-[2-( 1-methyl-2-pyrrolidi nyl)ethoxy]-", XP002751495, Database accession No. 1284856-24-1.
Database Registry [Online] Chemical Abstracts Service, Columbus, Ohio, US; Apr. 6, 2011 (Apr. 6, 2011), "1H-Pyrazole-4-methanamine, 1,3-dimethyl-5-[2-(1-methyl-2-pyrrolidinyl) ethoxy]-", XP002751496, Database accession No. 1275824-05-9.
Database Registry [Online] Chemical Abstracts Service, Columbus, Ohio, US; Nov. 22, 2009 (Nov. 22, 2009), "1H-Pyrazole-5-methanamine, N-[(1-ethyl-2-pyrrolidinyl)methyl]-1,3-dimethyl-", XP002751497, Database accession No. 1193211-04-9.
Database Registry [Online] Chemical Abstracts Service, Columbus, Ohio, US; Nov. 22, 2009 (Nov. 22, 2009), "1H-Pyrazole-5-methanamine, N-[ (1-ethyl-2-pyrrolidinyl)methyl]-1-phenyl-", XP002751498, Database accession No. 1193182-10-3.
Database Registry [Online] Chemical Abstracts Service, Columbus, Ohio, US; Jun. 14, 2009 (Jun. 14, 2009 ), "1H-Pyrazole-5-methanamine, N-[(1-ethyl-2-pyrrolidinyl) methyl]-1-methyl-", XP002751499, Database accession No. 1157110-36-5.
Database Registry [Online] Chemical Abstracts Service, Columbus, Ohio, US; Jun. 14, 2009 (Jun. 14, 2009 ), "1H-Pyrazole-4,5-diamine, N5-[(1-ethy1-2-pyrrolidinyl)methyl]-1,3-dimethyl-", XP002751500, Database accession No. 1157040-74-8.
Database Registry [Online] Chemical Abstracts Service, Columbus, Ohio, US; Mar. 7, 2008 (Mar. 7, 2008), "1H-Pyrazole-5-methanamine, 1-ethyl-N-(1-methyl-1Hpyrazol-5-yl)-3-(trifluoromethyl)-", XP002751501, Database accession No. 1006958-11-7.
Database Registry [Online] Chemical Abstracts Service, Columbus, Ohio, US; Mar. 7, 2008 (Mar. 7, 2008), "1H-Pyrazole-5-methanamine, 1-ethyl-N-[(1-ethyl-1H-pyrazol-5-yl)methyl]-3-(trifluoromethyl)-", XP002751502, Database accession No. 1006957-90-9.
Database Registry [Online] Chemical Abstracts Service, Columbus, Ohio, US; Mar. 7, 2008 (Mar. 7, 2008), "1H-Pyrazole-5-methanamine, N-[ (1-cyclopentyl-1H-pyrazol-5-yl)methyl]-1-ethyl-", XP002751503, Database accession No. 1006957-85-2.
Database Registry [Online] Chemical Abstracts Service, Columbus, Ohio, US; Mar. 7, 2008 (Mar. 7, 2008), "1H-Pyrazole-5-methanamine, 1-ethyl-N-[(1-ethyl-1H-pyrazol-5-yl)methyl]-", XP002751504, Database accession No. 1006957-80-7.
Database Registry [Online] Chemical Abstracts Service, Columbus, Ohio, US; Mar. 7, 2008 (Mar. 7, 2008), "1H-Pyrazole-5-methanamine, 1-ethyl-N-[(1-methyl-1Hpyrazol-5-yl)methyl]-3-(trifluoromethyl)-", XP002751505, Database accession No. 1006957-65-8.
Database Registry [Online] Chemical Abstracts Service, Columbus, Ohio, US; Mar. 7, 2008 (Mar. 7, 2008), "1H-Pyrazole-5-methanamine, N-[(1-cyclopentyl-1H-pyrazol-5-yl)methyl]-1-methyl-", XP002751506, Database accession No. 1006957-60-3.
Database Registry [Online] Chemical Abstracts Service, Columbus, Ohio, US; Mar. 7, 2008 (Mar. 7, 2008), "1H-Pyrazole-5-methanamine, 1-cyclopentyl-N-(1-methyl-1Hpyrazol-5-yl)-", XP002751507, Database accession No. 1006957-56-7.
Database Registry [Online] Chemical Abstracts Service, Columbus, Ohio, US; Mar. 7, 2008 (Mar. 7, 2008), "1H-Pyrazole-5-methanamine, 1-ethyl-N-(1-methyl-1Hpyrazol-5-yl)-", XP002751508, Database accession No. 1006957-03-4.
Database Registry [Online] Chemical Abstracts Service, Columbus, Ohio, US; Mar. 4, 2008 (Mar. 4, 2008), "1 H-Pyrazole-5-methanamine, N-[(1-ethyl-1 H-pyrazol-5-yl)methyl]-1-methyl-", XP002751509, Database accession No. 1006480-46-1.
Database Registry [Online] Chemical Abstracts Service, Columbus, Ohio, US; Mar. 4, 2008 (Mar. 4, 2008), "1H-Pyrazole-5-methanamine, N-[(1-ethyl-1H-pyrazol-5-yl)methyl]-1-methyl-3-(trifluoromethyl)-", XP002751510, Database accession No. 1006466-62-1.
Database Registry [Online] Chemical Abstracts Service, Columbus, Ohio, US; Mar. 4, 2008 (Mar. 4, 2008), "1H-Pyrazole-5-methanamine, 1-ethyl-N-[(1-propyl-1Hpyrazol-5-yl)methyl]-", XP002751511, Database accession No. 1006466-59-6.
Database Registry [Online] Chemical Abstracts Service, Columbus, Ohio, US; Mar. 4, 2008 (Mar. 4, 2008), "1H-Pyrazole-5-methanamine, 1-methyl-N-[(1-methyl-1Hpyrazol-5-yl)methyl]-3-(trifluoromethyl)-", XP002751512, Database accession No. 1006466-43-8.
Database Registry [Online] Chemical Abstracts Service, Columbus, Ohio, US; Mar. 4, 2008 (Mar. 4, 2008), "1H-Pyrazole-5-methanamine, 1-methyl-N-[(1-propyl-1Hpyrazol-5-yl)methyl]-", XP002751513, Database accession No. 1006466-39-2.
Database Registry [Online] Chemical Abstracts Service, Columbus, Ohio, US; Mar. 4, 2008 (Mar. 4, 2008), "1H-Pyrazole-5-methanamine, 1-methyl-N-(1-methyl-1Hpyrazol-5-yl)-3-(trifluoromethyl)-", XP002751514, Database accession No. 1006460-38-3.
Database Registry [Online] Chemical Abstracts Service, Columbus, Ohio, US; Mar. 4, 2008 (Mar. 4, 2008), "1H-Pyrazole-5-methanamine, N-(1-methy1-1H-pyrazol-5-yl)-1-propyl-", XP002751515, Database accession No. 1006459-91-1.
Database Registry [Online] Chemical Abstracts Service, Columbus, Ohio, US; Mar. 4, 2008 (Mar. 4, 2008), "1H-Pyrazole-5-methanamine, 1-methyl-N-(1-methyl-1Hpyrazol-5-yl)-", XP002751516, Database accession No. 1006459-42-2.
Database Registry [Online] Chemical Abstracts Service, Columbus, Ohio, US; Mar. 4, 2008 (Mar. 4, 2008), "1H-Pyrazole-5-methanamine, 1-methyl-N-[(1-methyl-1Hpyrazol-5-yl)methyl]-", XP002751517, Database accession No. 1006447-59-1.
Branch et al., Small molecule inhibitors of phagocytosis for treatment of immune cytopenias. 42nd Annual Scientific Meeting of the International Society for Experimental Hematology—Society for Hematology and Stem Cells, Vienna, Austria, Aug. 22-25, 2013. (Poster Presentation).
Branch et al., CIHR Website. Published Abstract. http://webapps.cihrirsc.gc.ca/cfdd/db_results_submit, Accessed on Feb. 5, 2013.
Bruno et al., "2-Phenyl-2,3-dihydro-1H-imidazo[1,2-b]pyrazole derivatives: New potent inhibitors of fMLP-induced neutrophil chemotaxis", *Bioorganic & Medicinal Chemistry Letters* 17 (2007) 3696-3701.
Carpenter et al., "Uptake by Mononuclear Phagocytes of Protein-Coated Bentonite Particles Stabilized With a Carbodiimide" *J. Immunol.* vol. 98. 4. 1967. pp. 844-853.
Chen et al., "TH1 and TH2 cytokine inhibition by 3,5-bis(trifluoromethyl)pyrazoles, a novel class of immunomodulators", *Cellular Immunology* 220 (2002) 134-142.
Crenshaw et al., "Interferon Inducing Activities of Derivatives of 1,3-Dimethyl-4-(3-dimethylaminopropylamino)-1H-pyrazolo[3,4-b]quinolone and Related Compounds". *J. Med. Chem.* vol. 19, No. 2. 1976. pp. 262-275.
Ditzel, "The K/BxN mouse : a model of human inflammatory arthritis". *Trends Mol. Med.* vol. 10. No. 1. 2004. pp. 40-45.

(56) References Cited

OTHER PUBLICATIONS

Foo et al., "Chemical treatment of anti-D results in improved efficacy for the inhivition of Fcγ receptor-mediated phagocytosis", *Transfusion.* vol. 47(2): 290-98, 2007.

Fusco et al., "Sintesi E Proprieta' Pharmacologiche di Copmosti Pirazolici". *FARMACO.* vol. 23 (10). 1968. pp. 919-944 (In Italian).

Hassan et al., "Phase Transfer Catalyzed C- vs O-alkylation of 3-methyl-1-phenyl-2-pyrazolin-5-one in the Absence or Presence of Carbon Disulphide". *Heterocycles.* vol. 45 (3). 1976. pp. 451-465.

Ishikawa et al., "A Pyrazole Derivative, YM-58483, Potently Inhibits Store-Operated Sustained Ca2+ Influx and IL-2 Production in T Lymphocytes", *The Journal of Immunology,* 2003, 170: 4441-4449.

Kinne et al., "Macrophages in rheumatoid arthritis". *Arthrisis Res.* vol. 2. 2000. pp. 189-202.

Lupo et al., "Synthèse et propriétés ionophores de coronands hétérocycliques I. Macrocycles a unités monopyrazoliques". *Bulletin De La Société Chimique De France.* vol. 2. No. 11-12. 1984. pp. 464-472. (English Abstract).

Majeed et al., "Role of Src Kinases and Syk in Fcgamma Receptor-Mediated Phagocytosis and Phagosome-Lysosome Fusion", *J Leukoc Biol.* Nov. 2001;70 (5):801-11.

Musante et al., "The Reactivity of the Carbonyl Group. I. Action of Arylhydrazines on Polyketones". *Gazzetta Chimica Italiana.* vol. 79. 1949. pp. 666-678 *(In Italian)*.

Packham et al., "Alteration of the Response of Platelets to Surface Stimuli by Pyrazole Compounds", *The journal of Experimental Medicine,* 1967, vol. 126, 171-190.

Petz et al., *Immune Hemolytic Anemias.* 2nd Ed., Churchill Livingstone/ Elsevier Science. 2004.

Psaila et al., "Fc receptors in immune thrombocytopenias: a target for immunomodulation?", *J. Clin. Invest.* vol. 118. No. 8. 2008. pp. 2677-2681.

Purohit et al., "Disulfide linked pyrazole derivatives inhibit phagocytosis of opsonized blood cells". *Bioorganic & Medicinal Chemistry Letters* 23. (2013). pp. 2324-2327.

Rampersad et al., "Chemical compounds that target thiol-disulfide groups on mononuclear phagocytes inhibit immune mediated phagocytosis of red blood cells." *Transfusion.* vol. 45. 3. 2005. pp. 384-393.

Sahaf et al., "Lymphocyte surface thiol levels". *Proc. Natl. Acad. Sci.* vol. 100. 7. 2003. pp. 4001-4005.

Siragam et al., "Can antibodies with specificity for soluble antigens mimic the therapeutic effects of intravenous IgG in the treatment of autoimmune disease?", *J. Clin. Invest.* vol. 115. 2005. pp. 155-160.

Wilkins et al., *Illustrated Pathology of the Spleen.* 2000. p. 55.

Revill et al., "Eitrombopag". *Drugs of the Future.* vol. 31. No. 9. 2006. pp. 767-770.

* cited by examiner

PYRAZOLE DERIVATIVES AND THEIR USES THEREOF

CROSS-REFERENCE TO RELATED APPLICATIONS

This application is a national phase application under 35 U.S.C. § 371 of International Application No. PCT/CA2014/050222 filed 12 Mar. 2014, which claims priority to U.S. Provisional Application No. 61/778,884 filed 13 Mar. 2013 and U.S. Provisional Application No. 61/778,865 filed 13 Mar. 2013. The entire contents of each of the above—referenced disclosures is specifically incorporated by reference herein without disclaimer.

BACKGROUND OF THE DISCLOSURE

Thrombocytes, or platelets, are anucleate and an important class of circulating blood cells that maintain haemostasis. A normal platelet count for an adult human is in the range of 150,000 to 450,000 per uL of blood. When the platelet count drops below 150,000 per μL of blood, it is defined as thrombocytopenia. A common pathophysiologic mechanism leading to thrombocytopenia is a disproportionate amount of consumption or destruction and loss of platelets from circulation compared to their rate of production. This most often occurs when autologous antibodies that recognize the endogenous platelets are produced in response to unknown stimuli, and these autoantibodies bind to, or opsonize the autologous platelets and are involved in their destruction, usually in the spleen or liver by tissue macrophages. This leads to the clinical disease known as immune thrombocytopenia (ITP).

Monocyte-macrophages recognize these opsonised platelets via a receptor on their outer surface called the Fc receptor (FcR) and clear them from circulation by a process called phagocytosis. ITP can be treated by reducing platelet destruction or by increasing platelet production. Current treatments for ITP include corticosteroids, rituximab, intravenous immunoglobulins (IVIG and anti-D), administration of thrombopoietin (TPO) receptor agonists, and surgical measures such as splenectomy. There are no treatments that have been proven to directly interfere with the opsonized platelet recognition by FcRs on monocyte-macrophages. Existing therapies have inherent limitations and challenges, such as the toxicities associated with immunosuppressant rituximab, relapse of ITP following discontinuation of the TPO receptor agonist treatment, and possible severe anemia and/or exposure to blood-borne infections from human plasma-derived IVIG.

Foo et al (*Transfusion*. 2007, 47 (2), 290-298) and Rampersad et al (*Transfusion*. 2005, 45 (3), 384-393) screened several small molecules carrying sulfhydryl and disulfide groups on aromatic and aliphatic compounds for their ability to inhibit the FcR-mediated phagocytosis of opsonized platelets by macrophages. It was hypothesized that these molecules would interact with the sulfhydryl or disulfide groups on the cell surface of human mononuclear phagocytes and inhibit the phagocytosis of opsonized red blood cells (RBC). This is based on the premise that cell surface proteins of monocyte-macrophages carry sulfhydryl and disulfide groups that play an important role in endocytic-phagocytic function, and small molecules carrying such groups would function as antagonists to the phagocytosis process (see Carpenter, R. R. et al *J. Immunol.* 1967, 98 (4), 844-853 and Sahaf, B. et al. *Proc. Natl. Acad. Sci.* 2003, 100 (7), 4001-4005).

SUMMARY OF THE INVENTION

In one aspect, the disclosure provides a compound of formula:

or a pharmaceutically acceptable salt thereof; wherein
U is an alkylene residue of 1-5 members, wherein one or two non-consecutive carbon atom is optionally independently replaced by O or NR10;
Q is wherein each R1 is independently H, alkyl, amino or halogen;
each R2 is independently H, alkyl, amino or halogen;
each R3 is independently aryl, -alkyl-aryl, cycloalkyl, -alkyl-cycloalkyl or substituted alkyl; and
R4 is hydroxyl, hydroxyalkyl or halogen;
R10 is H or a lower alkyl;
wherein each of the alkyl and aryl is optionally substituted.

In one aspect, the disclosure provides a method for treating or preventing a method for the prevention, treatment and/or alleviation of one or more autoimmune or alloimmune disease comprising administering to a subject in need thereof a therapeutically effective amount of a compound as defined herein In one aspect, the disclosure provides a pharmaceutical composition comprising a therapeutically effective amount of a compound as defined herein in combination with one or more pharmaceutically acceptable carrier or excipient.

In one aspect, the disclosure provides a combination comprising a therapeutically effective amount of a compound, as defined herein, and a therapeutically effective amount of at least one or more therapeutic agents useful in the method of the present disclosure.

In further embodiments, there is provided uses, compositions for use and compounds for use consistent with the method claims provided above.

DETAILED DESCRIPTION

In one embodiment, the disclosure provides a compound of formula:

I or a pharmaceutically acceptable salt thereof; wherein
U is an alkylene residue of 1-5 members, wherein one or two non-consecutive carbon atom is optionally independently replaced by O or NR10;
Q is wherein each R1 is independently H, alkyl, amino or halogen;
each R2 is independently H, alkyl, amino or halogen;
each R3 is independently aryl, cycloalkyl, or -alkyl-cycloalkyl; and
R4 is hydroxyl;
wherein each of the alkyl and aryl is optionally substituted.

In one embodiment, the disclosure provides a compound of formula:

I or a pharmaceutically acceptable salt thereof; wherein
U is an alkylene residue of 1-5 members, wherein one or two non-consecutive carbon atom is optionally independently replaced by O or NR10;
Q is wherein each R1 is independently H, alkyl, amino or halogen;
each R2 is independently H, alkyl, amino or halogen;
each R3 is independently aryl, -alkyl-aryl, cycloalkyl, -alkyl-cycloalkyl or substituted alkyl;
R4 is hydroxyl, hydroxyalkyl or halogen;
R10 is H or a lower alkyl;
wherein each of the alkyl and aryl is optionally substituted.

In one embodiment, the disclosure provides a compound of formula

II or a pharmaceutically acceptable salt thereof; wherein
U is an alkylene residue of 1-5 members, wherein one or two non-consecutive carbon atom is optionally independently replaced by O or NR10;
wherein each R1 is independently H, alkyl, amino or halogen;
each R2 is independently H, alkyl, amino or halogen;
each R3 is independently aryl, -alkyl-aryl, cycloalkyl, -alkyl-cycloalkyl or alkyl; and
R10 is H or a lower alkyl
wherein each of alkyl and aryl is optionally independently substituted.

In one embodiment, the compound has the formula:

II

In one embodiment, the compound has the formula:

III

In one embodiment, the compound has the formula:

IV

In one embodiment of any one of formulae I-IV, R2 is H.
In one embodiment of any one of formulae I-IV, R1 is H or alkyl.

In further embodiments of any one of formulae I-IV, R1 is C1-6 alkyl; R1 is C1-3 alkyl, R1 is C1-2 alkyl, R1 is methyl.

In one embodiment of any one of formulae I-IV, R3 is C6-10-aryl, —C1-2alkyl-C6-10aryl, 5-6 membered heterocycle, —C1-2alkyl-5-6 membered heterocycle, C5-6-cycloalkyl, —C1-2alkyl-C5-6cycloalkyl or C1-6 substituted alkyl.

In one embodiment of any one of formulae I-IV, R3 is C6-10-aryl, C5-6-cycloalkyl, or —C1-2alkyl-05-6cycloalkyl.

In one embodiment of any one of formulae I-IV, R3 is C6aryl, —C1-2alkyl-C6aryl, C5-6-cycloalkyl, —C1-2alkyl-05-6cycloalkyl or C1-6 substituted alkyl.

In one embodiment of any one of formulae I-IV, R3 is phenyl, $CH_2$-phenyl; cyclopentyl; cyclohexyl, $CH_2$-cyclopentyl; $CH_2$-cyclohexyl; $CH_2$—COOH or $CH_2CH_2NH_2$.

In further embodiments of any one of formulae I-IV:
U is an alkylene residue of 1-5 members
U is an alkylene residue of 2-5 carbon atoms;
U is an alkylene residue of 2-3 carbon atoms;
U is an alkylene residue of 2-5 members, wherein one carbon atom is replaced by O or NR10;
U is an alkylene residue of 2-3 members, wherein one carbon atom is replaced by O or NR10;
U is an alkylene residue of 2-3 members, wherein one carbon atom is replaced by 0;
U is an alkylene residue of 2-3 members, wherein one carbon atom is replaced by NR10.

In further embodiments of any one of formulae I-IV:
U is $CH_2$—$CH_2$
U is $CH_2$;
U is $CH_2$—O or O—$CH_2$; or
U is $CH_2$—NH—$CH_2$.

In one embodiment of any one of formulae I and III, R4 is hydroxyl, hydroxymethylene or a fluoride atom.

In one embodiment of any one of formulae I and III, R4 is hydroxyl.

In one embodiment, the disclosure provides a compound of formula

II or a pharmaceutically acceptable salt thereof; wherein
U is $CH_2$—$CH_2$, $CH_2$—O, O—$CH_2$; or $CH_2$—NH—$CH_2$, preferably $CH_2$—$CH_2$, $CH_2$—O;
each R1 is independently alkyl, preferably an alkyl of 1-3 carbon atoms, preferably a methyl;
R2 is H;
each R3 is independently aryl, -alkyl-aryl, cycloalkyl, -alkyl-cycloalkyl or alkyl; preferably phenyl, or benzyl, and
wherein each of alkyl and aryl is optionally independently substituted.

In one embodiment, the disclosure provides a compound of formula II, or a pharmaceutically acceptable salt thereof; wherein
U is $CH_2$—$CH_2$, $CH_2$—O, O—$CH_2$; or $CH_2$—NH—$CH_2$, preferably $CH_2$—$CH_2$, $CH_2$—O;
each R1 is independently alkyl, preferably an alkyl of 1-3 carbon atoms, preferably a methyl; R2 is H;
each R3 is independently aryl, cycloalkyl, or -alkyl-cycloalkyl preferably phenyl, and
wherein each of alkyl and aryl is optionally independently substituted.

In one embodiment, the disclosure provides a compound of formula II, or a pharmaceutically acceptable salt thereof; wherein
U is $CH_2$—$CH_2$, $CH_2$—O;
R1 is methyl;
R2 is H;
each R3 is independently phenyl, or benzyl, In one embodiment, the disclosure provides a compound of formula:

III or a pharmaceutically acceptable salt thereof; wherein
U is $CH_2$—$CH_2$, $CH_2$—O, O—$CH_2$; or $CH_2$—NH—$CH_2$, preferably $CH_2$—$CH_2$, $CH_2$—O;
R1 is independently alkyl, preferably an alkyl of 1-3 carbon atoms, preferably a methyl;
R2 is H;
R3 is independently aryl, -alkyl-aryl, cycloalkyl, -alkyl-cycloalkyl or alkyl; preferably phenyl, or benzyl; and
R4 is hydroxyl or hydroxyalkyl, preferably hydroxyl;
wherein each of the alkyl and aryl is optionally substituted.

In one embodiment, the disclosure provides a compound of formula III, or a pharmaceutically acceptable salt thereof; wherein
U is $CH_2$, $CH_2$—$CH_2$, $CH_2$—O;
R1 is an alkyl of 1-3 carbon atoms, preferably a methyl;
R2 is H;
R3 is aryl, or -alkyl-aryl, preferably phenyl, or benzyl, and
R4 is hydroxyl or hydroxyalkyl, preferably hydroxyl;
wherein each of the alkyl and aryl is optionally substituted.

In one embodiment, the disclosure provides a compound of formula III, or a pharmaceutically acceptable salt thereof; wherein
U is $CH_2$—$CH_2$, $CH_2$—O;
R1 is a methyl;
R2 is H;
R3 is phenyl, or benzyl; and
R4 is hydroxyl or hydroxyalkyl, preferably hydroxyl;
wherein each of the alkyl and aryl is optionally substituted In one embodiment, the disclosure provides a compound of formula III
or a pharmaceutically acceptable salt thereof; wherein
U is $CH_2$;
R1 is an alkyl of 1-3 carbon atoms, preferably a methyl;
R2 is H;
R3 is independently aryl, preferably phenyl, or benzyl; and
R4 is hydroxyl;
wherein each of the alkyl and aryl is optionally substituted.

In one embodiment, the disclosure provides a compound of formula III or a pharmaceutically acceptable salt thereof; wherein
U is CH$_2$;
R1 is an alkyl of 1-3 carbon atoms, preferably a methyl;
R2 is H;
R3 is independently aryl, preferably phenyl, and
R4 is hydroxyl;
wherein each of the alkyl and aryl is optionally substituted.

The term "alkyl" represents an optionally substituted linear or branched moiety. Examples of "alkyl" groups include but are not limited to methyl, ethyl, propyl, isopropyl, butyl, isobutyl, sec-butyl, tert-butyl, pentyl, isopentyl, neopentyl, tert-pentyl, hexyl, isohexyl or neohexyl. The term "alkyl" is also meant to include alkyls in which one or more hydrogen atoms are replaced by a halogen, i.e. an alkylhalide. In this application, fluoroalkyls are also particularly contemplated as alkylhalide.

The term "alkylene" has the same meaning as alkyl except that the group is bivalent.

The term "cycloalkyl" represents a carbocyclic moiety having 3 to 7 members, preferably 3-6 or more preferably 5-6. Examples of "cycloalkyl" groups include but are not limited to cyclopropyl, cyclobutyl, cyclopentyl, cyclohexyl and cycloheptyl.

As used herein, amino include amino which are unsubstituted such as —NH$_2$, or substituted with a suitable substituent such as substituted with one or two C1-6alkyl or aryl such as —NH(C$_{1-6}$alkyl), —N(C$_{1-6}$alkyl)$_2$, —N(C$_{1-6}$alkyl)(aryl) and —N(aryl)$_2$.

The term "aryl" represents an optionally substituted carbocyclic moiety containing at least one benzenoid-type ring (i.e., may be monocyclic or polycyclic), Examples include but are not limited to phenyl, tolyl, dimethylphenyl, aminophenyl, anilinyl, naphthyl, anthryl, phenanthryl or biphenyl.

The term "alkylaryl" represents an optionally substituted aryl group attached to the adjacent atom by an alkyl. Examples include but are not limited to benzyl, benzhydryl, trityl, phenethyl, 3-phenylpropyl, 2-phenylpropyl, 4-phenylbutyl and naphthylmethyl.

"Halogen atom" is specifically a fluorine atom, chlorine atom, bromine atom or iodine atom. Preferably the halogen is a fluorine atom.

The terms "optionally substituted" or "optional substituent" represent at each occurrence and independently, one or more halogen, amino, amidino, amido, azido, cyano, guanido, hydroxyl, nitro, nitroso, urea, OS(O)$_2$Rm (wherein Rm is selected from C1-6alkyl, C6-10aryl or 3-10 membered heterocycle), OS(O)$_2$ORn (wherein Rn is selected from H, C1-6alkyl, C6-10aryl or 3-10 membered heterocycle), S(O)$_2$ORp (wherein Rp is selected from H, C1-6alkyl, C6-10aryl and 3-10 membered heterocycle), S(O)$_{0-2}$Rq (wherein Rq is selected from H, C1-6alkyl, C6-10aryl or 3-10 membered heterocycle), OP(O)ORsORt, P(O)ORsORt (wherein Rs and Rt are each independently selected from H or C1-6alkyl), C1-6alkyl, hydroxyC1-6alkyl, C1-6heteroalkyl, C3-7cycloalkyl, C3-7cycloalkenyl, C6-10aryl-C1-6alkyl, C6-10aryl, C1-6alkoxy, C3-7cycloalkyloxy, C3-7cycloalkenyloxy, C6-10aryl-C1-6alkyloxy, C6-10aryloxy, 3-10 membered heterocycle, C(O)Ru (wherein Ru is selected from H, C1-6alkyl, C6-10aryl, C6-10aryl-C1-6alkyl or 3-10 membered heterocycle), C(O)ORv (wherein Rv is selected from H, C1-6alkyl, C6-10aryl, C6-10aryl-C1-6alkyl or 3-10 membered heterocycle), NRx-C(O)Rw (wherein Rx is H or C1-6alkyl and Rw is selected from H, C1-6alkyl, C6-10aryl, C6-10aryl-C1-6alkyl or 3-10 membered heterocycle, or Rx and Rw are taken together with the atoms to which they are attached to form a 3 to 10 membered heterocycle) or SO$_2$NRyRz (wherein Ry and Rz are each independently selected from H, C1-6alkyl, C6-10aryl, C3-10heterocycle or C6-10aryl-C1-6alkyl). In one embodiment, the term "optional substituent" represents halogen, amino, C1-6alkyl, C3-7cycloalkyl, carboxy, cyano, hydroxyl, nitro.

The term "independently" means that a definition can be the same or a different for each item.

When there is a nitrogen atom present, the nitrogen atom can be at different oxidation levels, i.e. N or NO. All such oxidation levels are within the scope of the present invention.

The excipient(s) or carrier(s) must be "pharmaceutically acceptable" in the sense of being compatible with the other ingredients of the formulation and not being deleterious to the recipient thereof. Standard accepted excipient(s) or carrier(s) are well known to skilled practitioners and described in numerous textbooks.

The following examples are provided to further illustrate details for the preparation and use of the compounds of the present invention. They are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus.

General. All solvents and reagents were obtained from commercial sources. Column chromatography purifications were performed on Biotage™ flash chromatography system using normal silica gel (60 Å, 70-230 mesh) and reverse-phase (C18) cartridges. Reactions were monitored by thin layer chromatography Merck. NMR spectra were recorded on Bruker™ spectrometer (400 MHz for $^1$H). Chemical shifts are reported in δ ppm using residual solvent peak as the reference for the $^1$H NMR spectra. Purity of the synthesized compounds was determined by Waters™ LC-MS system (Waters™ 2545 binary gradient module) including eluting system. Mass spectra (ESI) were recorded on a Waters™ LC/MS system equipped with a Waters™ 3100 mass detector.

EXAMPLE 1

Scheme 1.

(E)-1,1,1-Trichloro-4-methoxypent-3-en-2-one (8). In a flame dried flask, a solution of 2-methoxy propene (1.29 g) and pyridine (1.41 g) was cooled to 0° C. The ionic liquid, 1-butyl-3-methyl-imidazolium hexafluorophospahte (BMIM.PF6) (508 mg) was added to it and allowed to stir at 0° C. for 5 min. The above reaction mixture of enol ether, pyridine and ionic fluid was added dropwise to trichloroacetyl chloride (3.26 g) at 0° C. After the addition, the reaction was warmed to room temperature and allowed to stir for an additional 1 h. Reaction mixture was then diluted with diethyl ether, washed with water, brine and dried over $Na_2SO_4$. Organic layer was evaporated under reduced pressure to afford brown oil 8.

3-Methyl-1-phenyl-5-(trichloromethyl)-1H-pyrazole (9). To a Biotage™ Initiator microwave reaction vial containing a Teflon stirrer bar, β-methoxyvinyl trichloromethyl ketone (8) (442 mg), phenyl hydrazine (220 mg) and anhydrous toluene (5 mL) was added. The vial was capped and the reaction mixture was transferred to the microwave and irradiated at 85° C. for 5 min with cooling activated. The reaction solvent was evaporated under reduced pressure. The resulting crude was then purified by flash chromatography on silica gel using gradient 0-4% EtOAc-Hexanes to afford 9.

Ethyl 3-methyl-1-phenyl-1H-pyrazole-5-carboxylate (10). To a solution of compound 9 (750 mg) in ethanol (5 mL) pyridine (647 mg) was added and refluxed for 2 h. Reaction was monitored by TLC. Reaction was cooled to room temperature and solvent was evaporated under reduced pressure. The reaction crude was then diluted with DCM, washed with 10% HCl and dried over $Na_2SO_4$. Organic layer was evaporated to obtain compound 10

(3-Methyl-1-phenyl-1H-pyrazol-5-yl)methanol (11). To a suspension of LAH (229.97 mg) in anhydrous tetrahydrofuran (THF), a THF solution of compound 10 (696 mg) was added dropwise at 0° C. After the addition, the reaction was warmed to room temperature and allowed to stir for an additional 30 min. Reaction was then cooled to 0° C. and quenched with a saturated solution of $Na_2SO_4$. The resultant precipitate was filtered off under vacuum and the filtrate was evaporated to dryness to obtain 11. $^1$H NMR (CDCl$_3$) δ 2.34 (s, 3H), 4.65 (d, J=5.52 Hz, 2H), 6.26 (s, 1H), 7.36 (dd, J=16.00, 8.00 Hz, 1H), 7.46 (dd, J=16.00, 8.00 Hz, 2H), 7.58 (d, J=7.53 Hz, 1H).

5-(Bromomethyl)-3-methyl-1-phenyl-1H-pyrazole (12). To a solution of compound 11 (92 mg) in toluene, phosphorus tribromide (66.15 mg) was added at room temperature. Reaction was then refluxed for 2 h, cooled to room temperature and neutralized with saturated NaHCO$_3$ solution. Aqueous layer was extracted with DCM. Organic layer was dried over $Na_2SO_4$ and evaporated to yield compound 12

(3-Methyl-1-phenyl-1H-pyrazol-5-yl)methyl methanesulfonate (13). To a solution of compound 11 (50 mg), triethylamine (80.59 mg) in anhydrous DCM (3 mL) methanesulfonyl chloride (45.7 mg) was added drop wise at 0° C. After the addition, reaction mixture was refluxed for 2 h. The reaction was then cooled to room temperature, diluted with DCM (12 mL), washed with a saturated NaHCO$_3$ solution and dried over $Na_2SO_4$. Organic layer was evaporated to dryness to give compound 13. Intermediate 8 was used immediately for the next step.

EXAMPLE 2

Scheme 2.

1,2-Bis(3-methyl-1-phenyl-1H-pyrazol-5-yl)ethane (14). To an oven dried Biotage™ Initiator microwave reaction vial containing a Teflon stir bar, magnesium turnings (10.5 mg) were added, vial was capped and purged with nitrogen. Anhydrous THF (2 mL) was added to the reaction vial. A solution of compound 12 (104 mg) in anhydrous THF (1 mL) was added to above suspension. The reaction mixture was transferred to the microwave and irradiated at 100° C. with cooling activated. The reaction was then allowed to stir at room temperature for 42 h. On completion, the reaction was quenched with a saturated solution of ammonium chloride at 0° C. Aqueous layer was then extracted with EtOAc. Organic layer was washed with brine, dried over $Na_2SO_4$ and evaporated under reduced pressure. The resulting crude was then purified by flash chromatography on silica gel using gradient 0-30% EtOAc-Hexanes to afford compound 14. $^1$H NMR (CDCl$_3$) δ: 2.27 (s, 6H), 2.86 (s, 4H), 5.91 (s, 2H), 7.35-7.42 (m, 10 H). MS ESI (+ve) for $C_{22}H_{22}N_4$ (M+H$^+$) calculated 343.302, found 343.321.

EXAMPLE 3

Scheme 3.

3-Methyl-5-((3-methyl-1-phenyl-1H-pyrazol-5-yl)methoxy)-1-phenyl-1H-pyrazole (15). A suspension of edaravone (19) (41.6 mg) and cesium carbonate (260 mg) in anhydrous ACN (3 mL) was allowed to stir at room temperature for 5 min. Compound 13 synthesized from 11 (50 mg) was dissolved in 2 mL of anhydrous AcCN. The solution of 13 was added to the above reaction suspension and heated to 60° C. for 2 h. On completion, reaction mixture was cooled and filtered off. The resultant filtrate was adsorbed over silica and purified by flash chromatography on silica gel to obtain compound 15 (12 mg). $^1$H NMR (CDCl$_3$) δ 2.26 (s, 3H), 2.35 (s, 3H), 5.03 (s, 2H), 5.50 (s, 1H), 6.33 (s, 1H), 7.20 (m, 1H), 7.32-7.45 (m, 7H), 7.50-7.53 (m, 2H). MS ESI (+ve) for C$_{21}$H$_{20}$N$_4$O (M+H$^+$): calculated 345.172, found 345.302.

EXAMPLE 4

Scheme 4

2-((3-Methyl-1-phenyl-1H-pyrazol-5-yl)methyl)isoindoline-1,3-dione (16). To a reaction mixture of compound 11 (100 mg), triphenylphosphine (167 mg) and phthalimide (78.12 mg) in anhydrous THF (5 mL) was added diethyl azodicarboxylate (138.62 mg) at 0° C. After stirring the reaction at room temperature for 48 h, the solvent was evaporated under vacuum and the resultant crude was purified by flash chromatography using gradient 1-30% EtOAc-Hexanes to give compound 16 (158 mg).

(3-Methyl-1-phenyl-1H-pyrazol-5-yl)methanamine (17). To a solution of compound 16 (158 mg) in methanol (2 mL) was added hydrazine hydrate (125 mg) at 0° C. The reaction mixture was stirred overnight. The reaction solvent was evaporated under vacuum and the resultant crude was suspended in the methanol (2 mL). The white insoluble precipitate was filtered off and the filtrate was evaporated to afford compound 17 (79 mg).

Bis((3-methyl-1-phenyl-1H-pyrazol-5-yl)methyl)amine (18). To a flask containing suspension of compound 17 (58 mg, 0.26 mmol) and potassium carbonate (112 mg) in anhydrous ACN (2 mL) was added a solution of compound 12, synthesized from precursor 11 (50 mg), in ACN (1 mL) at room temperature. The reaction mixture was then heated to 60° C. for 2 h. On cooling the reaction mixture was concentrated under vacuum and purified by flash chromatography using gradient 10-80% EtOAc-Hexanes to obtain compound 18 (41 mg). $^1$H NMR (CDCl$_3$) δ 2.15 (s, 3H), 2.33 (s, 3H), 2.95 (br t, 2H), 3.82 (t, J=6 Hz, 2H), 4.96 (s, 2H), 5.31 (s, 1H), 6.32 (s, 1H), 7.34-7.48 (m, 5H).

EXAMPLE 5

Scheme 5

1,2-Bis(3-methyl-1-phenyl-1H-pyrazol-5-yloxy)ethane (20). To a suspension of edaravone (19) (402 mg) and cesium carbonate (1800 mg) in anhydrous ACN (5 mL) 1,2-dibromoethane (217 mg) was added. The reaction mixture was heated to 60° C. for overnight. The reaction was filtered and the filtrate was concentrated under vacuum. The resultant crude was purified by flash chromatography to obtain product 20. $^1$H NMR (CDCl$_3$) δ 2.26 (s, 6H), 4.32 (s, 4H), 5.50 (s, 2H), 7.17-7.22 (m, 2H), 7.27-7.32 (m, 4H), 7.60-7.63 (m, 4H). MS ESI (+ve) for C$_{22}$H$_{22}$N$_4$O$_2$ (M+H$^+$): calculated 375.182, found 375.301.

EXAMPLE 6

Scheme 6

5-Chloro-3-methyl-1-phenyl-1H-pyrazole (21). To a flask containing edaravone (19) (2 g) phosphorus oxychloride (3 mL) was added and refluxed for 2 h. On cooling the reaction mixture was poured over crushed ice. The aqueous layer was extracted with EtOAc which was then washed with brine, dried over Na$_2$SO$_4$ and concentrated under vacuum. The resultant crude was passed through a short column of silica gel to give compound 21 (1.8 g).

5-Chloro-3-methyl-4-nitro-1-phenyl-1H-pyrazole (22). To a round bottom flask containing compound 21 (110 mg) was added acetic anhydride (1.5 mL) and cooled to 0° C. Concentrated nitric acid (1 mL) was then added dropwise. The reaction mixture was warmed up to room temperature and stirred for 4 h. The reaction solution was then poured over crushed ice. The water insoluble yellow precipitate was collected and purified by flash chromatography to obtain compound 22 (126 mg).

3-Methyl-5-(3-methyl-1-phenyl-1H-pyrazol-5-yloxy)-4-nitro-1-phenyl-1H-pyrazole (23). In a Biotage™ Initiator microwave reaction vial containing a Teflon stirrer bar, compound 22 (50 mg), edaravone (19) (36.6 mg) and potassium carbonate (87 mg) were added, and the vial was capped and purged with nitrogen. To this reaction vial anhydrous DMF (0.5 mL) was added and subjected to microwave irradiation at 80° C. high absorption for 12 min with cooling activated. The reaction crude was then purified by flash chromatography to afford compound 23 (65 mg).

3-Methyl-5-(3-methyl-1-phenyl-1H-pyrazol-5-yloxy)-1-phenyl-1H-pyrazol-4-amine (24). To a solution of compound 23 (20 mg) in conc. HCl (1 ml) tin (II) chloride dihydrate (60.10 mg) dissolved in conc. HCl (1 mL) was added to it at 0° C. On completion, the reaction mixture was poured over crushed ice and neutralized with a saturated solution of NaHCO$_3$. The organic product was extracted with EtOAc, then washed with brine, dried over Na$_2$SO$_4$ and concentrated under vacuum. The resultant crude was purified by flash chromatography to obtain product 24 (8.3 mg). $^1$H NMR (CDCl$_3$) δ 2.26 (s, 3H), 2.27 (s, 3H), 2.63 9 s, br, 2H), 5.50 (s, 1H), 7.20-7.23 (m, 1H), 7.28-7.34 (m, 3H), 7.40-7.44 (m, 2H), 7.47 (d, J=7.84 Hz, 2H), 7.64 (d, J=7.60 Hz, 2H). MS ESI (+ve) for C$_{20}$H$_{19}$N$_5$O: calculated 346.167, found 346.270 for (M+H$^+$).

EXAMPLE 7

Scheme 7

(4-Nitrophenyl)hydrazine dihydrochloride salt (26). p-Nitroaniline (25) (1.4 g) was dissolved in conc. HCl (2 mL) and cooled to 0° C. A solution of sodium nitrite (717 mg) in ice-cooled water (4 mL) was added drop wise to above acidic reaction mixture and stirred for 1 h at 0° C. Ice-cooled solution of stannous chloride (4.7 g) in conc. HCl (2 mL) was added slowly to above diazonium reaction mixture. The reaction was stirred at 0° C. for 2 h. The yellow-orange precipitate was collected and washed thoroughly with ice-cold water until the filtrate pH was neutral. Collected precipitate was dried overnight on high vacuum to give dihydrochloride salt of compound 26 (640 mg).

3-Methyl-1-(4-nitrophenyl)-1H-pyrazol-5(4H)-one (27). To a solution of compound 26 (219 mg) in glacial acetic acid (2 mL) ethyl-3-oxobutanoate (167 mg) was added and refluxed for 3 h. The reaction mixture was cooled to 0° C. and diethyl ether (5 mL) was added to it. After stirring for 1 h at 0° C., the reaction mixture was filtered and the collected precipitate was washed with diethyl ether. The precipitate was then purified by flash chromatography on silica gel using gradient 10-80% EtOAc-Hexanes to afford compound 27

3-Methyl-5-({[3-methyl-1-(4-nitrophenyl)-1H-pyrazol-5-yl]oxy}methyl)-1-phenyl-1H-pyrazole (28). Compound 27 (113 mg) and cesium carbonate (334 mg) were suspended in anhydrous ACN (2 mL). Compound 12 synthesized from compound 11 (100 mg) was dissolved in 2 mL of anhydrous ACN and added drop wise to above reaction suspension. The reaction was then heated to 60° C. for overnight. The reaction solvent was removed by rotary evaporation and the resulting crude was purified by flash chromatography on silica gel to afford product 28.

EXAMPLE 8

Ethyl 3-methyl-1H-pyrazole-5-carboxylate (29). To a stirred suspension of hydrazine mono hydrochloride (642 mg) in ethanol (5 mL) was added β-methoxy vinyl trichloromethylketone (8) (1.7 g) at room temperature. After refluxing for 4 h, the reaction mixture was filtered, solvent was removed under vacuum and the resultant crude was recrystallized to obtain product 29

Ethyl 1-benzyl-3-methyl-1H-pyrazole-5-carboxylate (30). To a flask containing suspension of compound 29 (313 mgl) and potassium carbonate (842 mg) in anhydrous AcCN (4 mL) benzyl bromide (347 mg) was added at 0° C. The reaction mixture was then stirred at room temperature overnight. The reaction solvent was removed under vacuum and the resultant residue was purified by flash chromatography to afford compound 30 (114 mg)

(1-Benzyl-3-methyl-1H-pyrazol-5-yl)methanol (31). To a suspension of LAH (53.12 mg) in anhydrous THF (3 mL) at 0° C., a THF solution of compound 30 (112 mg) was added drop wise, followed by stirring the reaction at room temperature for 30 min. It was then cooled to 0° C. and quenched with a saturated solution of $Na_2SO_4$. The squelched reaction was filtered and filtrate was evaporated under vacuum to yield compound 31.

1-Benzyl-3-methyl-5-((3-methyl-1-phenyl-1H-pyrazol-5-yloxy)methyl)-1H-pyrazole (32). To a solution of compound 31 (64 mg), triethylamine (95.84 mg) in anhydrous DCM (3 mL) methanesulfonyl chloride (54 mg) was added drop wise at 0° C. After the addition, reaction mixture was refluxed for 2 h. The reaction was then cooled to room temperature, diluted with DCM (12 mL), washed with a saturated $NaHCO_3$ solution and dried over $Na_2SO_4$. Organic layer was evaporated to dryness to give mesylated derivative of 31. Crude mesylated derivative of 31 was dissolved in anhydrous ACN (2 mL) and added to a flask containing suspension of edaravone (19) (55 mg) and cesium carbonate (309 mg) in anhydrous ACN (3 mL). After heating the reaction at 60° C. for 4 h, it was cooled, solvent was removed under vacuum and the resultant crude was purified by flash chromatography to afford product 32 (40 mg) $^1$H NMR ($CDCl_3$) δ 2.26 (s, 3H), 2.29 (s, 3H), 4.90 (s, 2H), 5.25 (s, 2H), 5.47 (s, 1H), 6.15 (s, 1H), 7.00-7.02 (m, 2H), 7.21-7.24 (m, 4H), 7.33-7.37 (m, 2H), 7.52-7.54 (m, 2H). MS ESI (+ve) for $C_{22}H_{22}N_4O$ was calculated 359.187, and found 359.285 for $(M+H^+)$.

EXAMPLE 9

36

37

1-(Pivaloyloxy)-2-(propan-2-ylidene) hydrazine (33). A suspension of t-butyl carbazate (1000 mg) and magnesium sulfate (182 mg) in anhydrous acetone (7.5 mL) with catalytic amount of acetic acid (18 mg) was refluxed for 1 h. The reaction mixture was then cooled to room temperature and filtered. Organic filtrate was evaporated under reduced pressure to afford white crystalline solid 33 (1.23 g).

tert-Butyl-1-(cyclohexylmethyl)-2-(propan-2-ylidene)hydrazinecarboxylate (34). A suspension of compound 33 (496 mg), potassium hydroxide (182 mg) and tetra butyl ammonium hydrogen sulfate (11 mg) in toluene (4 mL) was heated to 50° C. for 2 h with vigorous stirring. To above reaction mixture (bromomethyl)cyclohexane (639 mg) was added drop wise and heated to 80° C. After 2 h, the reaction mixture was cooled to room temperature and diluted with EtOAc, washed with water, brine and dried over $Na_2SO_4$. The solvent was removed by rotary evaporation to give product 34 (Mixture of rotamers)

(Cyclohexylmethyl)hydrazine dihydrochloride salt (35). To a flask containing compound 34 (800 mg) was added 2N HCl in THF (217 mg at room temperature. The reaction mixture was then refluxed for 2 h and after cooling the reaction solvent was evaporated under vacuum. The crude residue was dissolved in ethanol (3 mL) and cooled to 8° C. (cooled water bath). Diethyl ether was then added slowly to precipitate dihydrochloride salt 35.

1-(Cyclohexylmethyl)-3-methyl-1H-pyrazol-5(4H)-one (36). To a solution compound 35 (150 mg) in ethanol (3 mL), ethylacetoacetate (116 mg) was added and refluxed for 2 h. The solvent was removed by rotary evaporation and the resulting crude was purified by flash chromatography to afford compound 36

1-(Cyclohexylmethyl)-3-methyl-5-((3-methyl-1-phenyl-1H-pyrazol-5-yl)methoxy)-1H-pyrazole (37). Compound 36 (40 mg) and cesium carbonate (201 mg) were suspended in anhydrous AcCN (2 mL). Compound 12 (50 mg) was dissolved in 2 mL of anhydrous AcCN and added drop wise to above reaction suspension. The reaction was then heated to 60° C. overnight. The reaction solvent was removed and the resulting crude was purified to give product 37. $^1$H NMR ($CDCl_3$) δ: 0.80-0.98 (m, 2H) 1.05-1.29 (m, 5H) 1.58-1.87 (m, 5H) 2.18 (s, 3H) 2.37 (s, 3H) 3.62 (d, J=7.28 Hz, 2H) 4.94 (s, 2H) 5.30 (s, 1H) 6.34 (s, 1H) 7.33-7.56 (m, 5H). MS ESI (+ve) for $C_{22}H_{28}N_4O$ was calculated 365.234, and found 365.361 for (M+H$^+$).

EXAMPLE 10

Scheme 10 tert-Butyl 2-cyclopentylidenehydrazinecarboxylate (38). A suspension of tert-butyl carbazate (4.5 g) and cyclopentanone (2.8 g) in hexane (35 mL) was refluxed for 30 min. On completion, the reaction mixture was cooled and filtered. The white precipitate was collected and dried over vacuum to afford product 38.

Cyclopentylhydrazine ditrifluoroacetate salt (39). To a suspension of LAH (267 mg) in anhydrous THF (2 mL) at 0° C., a THF (2 mL) solution of compound 38 (700 mg) was added drop wise. After the addition, the reaction was warmed to room temperature and allowed to stir for additional 30 min. Reaction was then cooled to 0° C. and quenched with a saturated solution of $Na_2SO_4$. The resultant precipitate was filtered off under vacuum and the filtrate was evaporated to dryness. The resulting residue was then dissolved in DCM (4 mL) and cooled to 0° C. A mixture of TFA and DCM (1:1, 1 mL) was added to it and stirred at room temperature for 20 min. On completion, the reaction solvent was removed under vacuum to yield 39.

1-Cyclopentyl-3-methyl-1H-pyrazol-5(4H)-one (40). To a solution of compound 39 (932 mg) in ethanol (5 mL) ethylacetoacetate (49 mg) was added. The reaction mixture was then refluxed overnight. The reaction solvent was removed under vacuum and the resulting residue was purified by flash chromatography to give product 40.

1-Cyclopentyl-3-methyl-5-((3-methyl-1-phenyl-1H-pyrazol-5-yl)methoxy)-1H-pyrazole (41). Compound 40 (60 mg) and potassium carbonate (54 mg) were suspended in anhydrous DMF (1 mL). The reactant 13 synthesized from compound 11 (50 mg) was dissolved in 1 mL of anhydrous DMF and added drop wise to above reaction suspension. The reaction was then heated to 45° C. for 2 h. The reaction solvent was removed and the resulting crude was purified by flash chromatography to give the product 41. $^1$H NMR ($CDCl_3$) δ: 1.47-1.65 (m, 2H), 1.77-1.98 (m, 6H), 2.13-2.22 (m, 3H), 2.29-2.43 (m, 3H), 4.35-4.51 (m, 1H), 4.95 (s, 2H), 5.25-5.36 (m, 1H), 6.35 (s, 1H), 7.34-7.56 (m, 5H). MS ESI (+ve) for $C_{20}H_{24}N_4O$ was calculated 337.203, and found 337.343 for $(M+H^+)$.

EXAMPLE 11

Scheme 11

3-Methyl-1H-pyrazol-5-ol (42). To a suspension of hydrazine hydrate (2.6 g) in methanol (5 mL) ethyl-3-oxobutanoate (1.0 g) was added. The reaction mixture was then refluxed for 2 h. The reaction solvent was evaporated under vacuum to afford product 42.

2-(2-(5-Hydroxy-3-methyl-1H-pyrazol-1-yl)ethyl)isoindoline-1,3-dione (43). Compound 42 (500 mg) and N-(2-bromo ethyl)-phthalimide (1.3 g) were suspended in 1,4-dioxane (3 mL) in a Biotage Initiator microwave reaction vial containing a Teflon stir bar. The vial was capped and the reaction mixture was transferred to the microwave and irradiated at 180° C. at normal absorption with cooling activated. The reaction solvent was evaporated and the resulting crude was purified by flash chromatography on silica gel using gradient 0-10% MeOH-DCM to afford product 43.

Ethyl-2-(3-Methyl-5-oxo-4,5-dihydro-1H-pyrazol-1-yl) acetate (44). To a flask containing compound 42 (547 mg, 5.58 mmol) was added ethylbromoacetate (932.18 mg, 5.58 mmol) and refluxed for 4 h. Then, the reaction was cooled, diluted with ice-cooled water (2 mL), neutralized with cold saturated solution of $NaHCO_3$ and stirred for 15 min at room temperature. Aqueous reaction mixture was extracted with EtOAc. Organic layer was washed with brine, dried over $Na_2SO_4$ and removed by rotary evaporation. The resultant crude was then purified by flash chromatography on silica gel using gradient 0-10% MeOH-DCM to yield compound 44 as a white solid (138 mg, 0.79 mmol), yield 13%.

2-(2-(3-Methyl-5-((3-methyl-1-phenyl-1H-pyrazol-5-yl) methoxy)-1H-pyrazol-1-yl)ethyl) isoindoline-1,3-dione (45). Compound 43 (144 mg) and cesium carbonate (519 mg) were suspended in anhydrous AcCN (2 mL). Compound 12 synthesized from compound 11 (100 mg) was dissolved in 2 mL of anhydrous AcCN and added drop wise to above reaction suspension. The reaction was then heated to 60° C. overnight. The reaction solvent was removed by rotary evaporation and the resulting crude was purified by flash chromatography to afford product 45. $^1$H NMR $(CDCl_3)$ δ: 1.99 (s, 3H), 2.28 (s, 3H), 3.88-3.91 (t, J=5.7 Hz, 2H), 4.09-4.12 (t, J=5.2 Hz, 2H), 4.79 (s, 2H), 5.24 (s, 1H), 6.12 (s, 1H), 7.31-7.35 (m, 1H), 7.38-7.45 (m, 4H), 7.61-7.63 (m, 2H), 7.70-7.72 (m, 2H).

Ethyl-2-(3-methyl-5-((3-methyl-1-phenyl-1H-pyrazol-5-yl)methoxy)-1H-pyrazol-1-yl)acetate (46). Compound 44 (40 mg) and cesium carbonate (212 mg) were suspended in anhydrous ACN (2 mL). Compound 12 synthesized from compound 11 (41 mg) was dissolved in 2 mL of anhydrous AcCN and added drop wise to above reaction suspension. The reaction was then heated to 60° C. for 2 h. The reaction solvent was removed and the resulting crude was purified by flash chromatography to give product 46. $^1$H NMR $(CDCl_3)$ δ: 1.21-1.25 (t, J=7.12 Hz, 3H), 2.18 (s, 3H), 2.34 (s, 3H), 4.15-4.20 (q, J=7.12, 7.16 Hz, 2H), 4.58 (s, 2H), 4.96 (s, 2H), 5.35 (s, 1H), 6.33 (s, 1H), 7.34-7.38 (m, 1H), 7.42-7.48 (m, 4H).

2-(3-Methyl-5-((3-methyl-1-phenyl-1H-pyrazol-5-yl) methoxy)-1H-pyrazol-1-yl)ethanamine (47). To a solution of compound 45 (40 mg) in methanol (2 mL) hydrazine hydrate (102 mg) was added. The reaction was stirred overnight. The solvent was evaporated and the resulting crude was purified to give the product 47. $^1$H NMR $(CDCl_3)$ δ: 2.15 (s, 3H), 2.33 (s, 3H), 2.95 (br m, 2H), 3.81-3.84 (t, J=5.88 Hz, 2H), 4.96 (s, 2H), 5.31 (s, 1H), 6.32 (s, 1H), 7.34-7.37 (m, 1H), 7.41-7.48 (m, 4H).

2-(3-Methyl-5-((3-methyl-1-phenyl-1H-pyrazol-5-yl) methoxy)-1H-pyrazol-1-yl)acetic acid (48). Compound 46 (24 mg) was dissolved in a mixture of MeOH:THF (1:1) (2 mL). Lithium hydroxide (29 mg) was added to the reaction mixture at 0° C. The reaction was stirred overnight. The solvent was removed under vacuum, water (1 mL) was added and neutralized with 10% HCl at 0° C. Aqueous layer was extracted with EtOAc. Organic layer was removed and the crude was purified to obtain compound 48. $^1$H NMR $(CDCl_3)$ δ: 2.16 (s, 3H), 2.34 (s, 3H), 4.63 (s, 2H), 4.96 (s, 2H), 5.34 (s, 1H), 6.33 (s, 1H), 7.34-7.35 (m, 1H), 7.40-7.44 (m, 4H).

EXAMPLE 12

Scheme 12

50

3-Methyl-1H-pyrazol-5-ol (42). To a suspension of hydrazine hydrate (2.6 g) in methanol (5 mL) ethyl-3-oxobutanoate (1.0 g) was added. The reaction mixture was then refluxed for 2 h. The reaction solvent was evaporated to afford product 42 (1.92 g)

3-Methyl-5-((3-methyl-1H-pyrazol-5-yloxy)methyl)-1-phenyl-1H-pyrazole (49) and 3-methyl-1-((3-methyl-1-phenyl-1H-pyrazol-5-yl)methyl)-1H-pyrazol-5-ol (50). Compound 42 (104 mg) and cesium carbonate (346 mg) were suspended in anhydrous AcCN (2 mL). Compound 13 (200 mg) was dissolved in 2 mL of anhydrous AcCN and added drop wise to above reaction suspension. The reaction was stirred for 2 h at 80° C. The reaction solvent was removed and was purified by column chromatography to give products 49 and 50, as white solids. Compound 49, $^1$H NMR (CDCl$_3$) δ: 2.23 (s, 3H), 2.34 (s, 3H), 5.11 (s, 2H), 5.52 (s, 1H), 6.37 (s, 1H), 7.30-7.36 (m, 1H), 7.42 (t, J=7.91 Hz, 2H), 7.55 (d, J=7.53 Hz, 2H). Compound 50, $^1$H NMR (CDCl$_3$) δ: 1.92 (s, 3H), 2.28 (s, 3H), 5.00 (s, 2H), 5.40 (s, 1H), 5.97 (s, 1H), 7.32-7.58 (m, 5H). Compound 49, MS ESI (+ve) for $C_{15}H_{16}N_4O$ was calculated 312.182, and found 312.283 for (M+H$^+$). Compound 50, MS ESI (+ve) for $C_{15}H_{16}N_4O$ was calculated 327.140, and found 327.261 for (M+H$^+$).

EXAMPLE 13

Scheme 13

1-Benzyl-2-(bromomethyl)pyrrolidine (52). In a flask containing carbon tetrabromide (1.7 g) and triphenylphosphine (1.44 g) in anhydrous THF (5 mL) (1-benzylpyrrolidin-2-yl)methanol (700 mg) was added at 0° C. The reaction was allowed to stir at room temperature overnight. The reaction mixture was purified by column chromatography 1-10% EtOAc-Hexanes to yield compound 52

5-((1-Benzylpyrrolidin-2-yl)methoxy)-3-methyl-1-phenyl-1H-pyrazole (53). To a suspension of edaravone (34 mg) and potassium carbonate (81 mg) in anhydrous DMF (1 mL), compound 52 (50 mg) dissolved in DMF (1 mL) was added. The reaction was heated overnight at 50° C. On completion, the reaction was diluted with 5 mL of water. The aqueous layer was extracted with EtOAc and then washed with brine, dried over Na$_2$SO$_4$ and the organic layer was concentrated. The resulting crude was purified to afford compound 53 NMR (CDCl$_3$) δ: 1.24-1.74 (m, 3H), 1.96-2.01 (m, 1H), 2.24 and 2.26 (s, 3H), 2.30-2.38 (m, 2H), 2.90-3.00 and 3.49 (m, 2H), 3.53 and 3.99 (s, 2H), 3.90-4.29 (m, 1H), 5.37 and 5.44 (s, 1H), 7.17-7.47 (m, 8H), 7.66-7.75 (m, 2H). MS ESI (+ve) for $C_{22}H_{25}N_3O$ was calculated 348.208, and found 348.349 for (M+H$^+$).

The compounds as defined herein may include a chiral center which gives rise to enantiomers. The compounds may thus exist in the form of two different optical isomers, that is (+) or (−) enantiomers. All such enantiomers and mixtures thereof, including racemic or other ratio mixtures of individual enantiomers, are included within the scope of the invention. The single enantiomer can be obtained by methods well known to those of ordinary skill in the art, such as chiral HPLC, enzymatic resolution and chiral auxiliary derivatization.

It will also be appreciated that the compounds in accordance with the present disclosure can contain more than one chiral centre. The compounds of the present invention may thus exist in the form of different diastereomers. All such diastereomers and mixtures thereof are included within the scope of the invention. The single diastereomer can be obtained by methods well known in the art, such as HPLC, crystalisation and chromatography.

There is also provided pharmaceutically acceptable salts of the compounds described herein. What is meant by the term pharmaceutically acceptable salts of the compounds is that they are derived from pharmaceutically acceptable inorganic and organic acids and bases. Examples of suitable acids include but are not limited to hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids.

Other acids such as oxalic, while not in themselves pharmaceutically acceptable, may be useful as intermediates in obtaining the compounds of the invention and their pharmaceutically acceptable acid addition salts. Salts derived from appropriate bases include alkali metal, alkaline earth metal or ammonium salts. The salt(s) must be "acceptable" in the sense of not being deleterious to the recipient thereof.

EXAMPLE 14

Phagocytosis. Monocyte monolayer assay. The monocyte monolayer assay (MMA) was performed as previously described (Rampersad, G. C.; Suck, G; Sakac, D; Fahim, S; Foo, A; Denomme, G. A.; Langler, R. F.; Branch, D. R. Transfusion 2005, 45, 384; Foo, A. H.; Fletcher, S. P.; Langler, R. F.; Porter, C. H.; Branch, D. R. Transfusion 2007, 47, 290; Branch, D. R.; Gallagher, M. T.; Mison, A. P.; Sy Siok Hian, A. L.; Petz, L. D. Br. J. Haematol. 1984, 56, 19; Gallagher, M. T.; Branch, D. R.; Mison, A.; Petz, L. D. Exp. Hematol. 1983, 11, 82) in the above 4 references with slight modification. Briefly, peripheral blood mononuclear cells (PBMC) containing monocytes were isolated by ficoll-paque density gradient centrifugation and incubated overnight at 37° C. under 5% $CO_2$ atmosphere. PBMCs were then layered onto chamber slides (Labtek, Thermo Scienctific) and incubated at 37° C., 5% $CO_2$ for 1 hr to allow the monocytes to adhere. Following an aspiration of non-adherent cells, compounds were added at various concentrations to the adhered cells and further incubated for an additional hour. The compounds were aspirated and the monocytes treated with anti-D opsonized RBCs at the aforementioned incubation conditions for an additional 2 hrs. The slides were analyzed under phase microscopy for phagocytosis. A minimum of 100 monocytes were counted per sample and the number of observed RBCs that were phagocytosed were counted and normalized to a positive control to generate a phagocytosis index. Percent inhibition of phagocytosis was calculated as the percentage of control phagocytosis (phagocytosis of opsonized RBCs with compound diluent only).

Using the above-described assay, selected compounds provided the inhibition listed in table 1

TABLE 1

| Compound | Activity @ 5 micromolar (%) | SEM (%) |
|---|---|---|
| 15 | up to 14 | 8-11 |
| 14 | up to 16 | 10-11 |
| 18 | 20 | 14 |
| 20 | 4-14 | 3-12 |
| 23 | 12 | 8 |
| 24 | 2 | 4 |
| 28 | 2-16 | 6-33 |
| 37 | 33-45 | 5-15 |
| 41 | up to 17 | 2-9 |
| 47 | 5-33 | 2-16 |
| 48 | 4-10 | 5-10 |
| 49 | 6-26 | 4-11 |
| 50 | 27-58 | 4-14 |
| 53 | 5-15 | 14-16 |

EXAMPLE 15

Efficacy of Compound 50 Given IP or IV at Preventing ITP In Vivo

Figure 1:
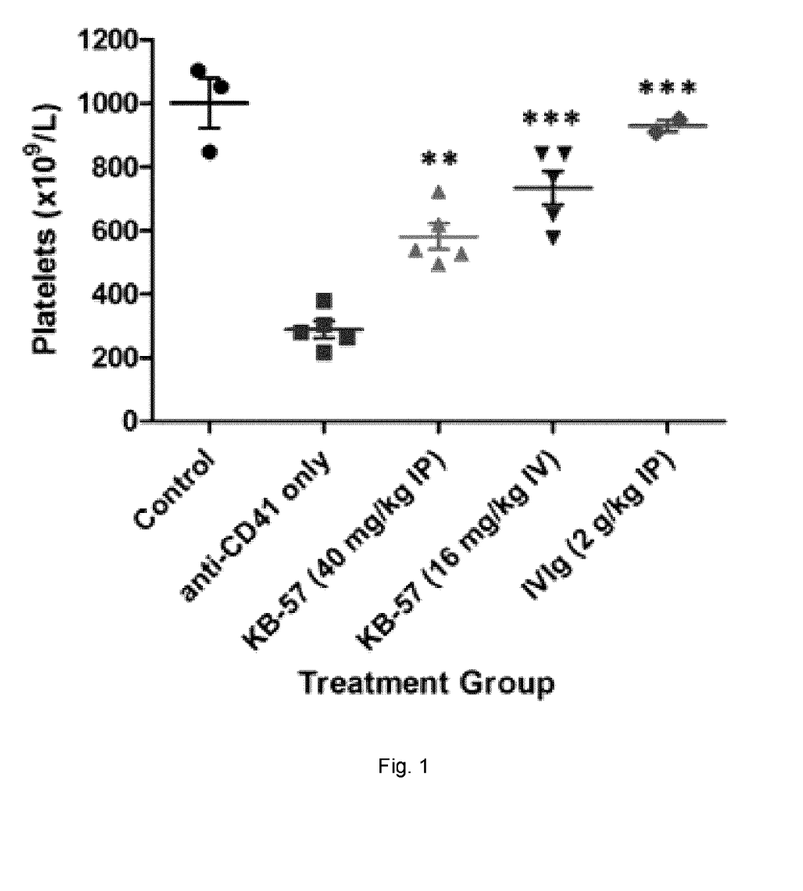
FIG. 1 is showing the efficacy of a compound of this disclosure given IP or IV at preventing ITP in vivo.

Compound 50 (designated KB-57 in the figure) ameliorates ITP in the preventive mouse model of ITP, previously published (Katsman Y, Foo A H, Leontyev D, Branch, D. R. *Improved mouse models for the study of treatment modalities for immune-mediated platelet destruction.* Transfusion 2010; 50:1285-1294.) which was modified slightly to use a constant dose of anti-platelet antibody. Mice (BALB/c) were treated with an anti-platelet antibody (rat anti-mouse CD41 using 1.4 µg constant dose) daily starting at Day 0 to induce ITP. Platelet counts at Day 2, when a nadir is reached in this model, are shown for untreated mice, mice treated with anti-CD41 only, mice treated with IVIG (1 g/kg) (positive control for ITP amelioration), and mice treated with Compound 50 i.p. (40 mg/kg) or i.v. (16 mg/kg). Treatment groups: n=5 mice per group; control: n=3. Statistical significance by one-way ANOVA with Dunnett posthoc test and is indicated:  $p<0.01$; * $p<0.001$.

EXAMPLE 16

Efficacy of Compound 50 Given Subcutaneously at Preventing ITP In Vivo

Figure 2:
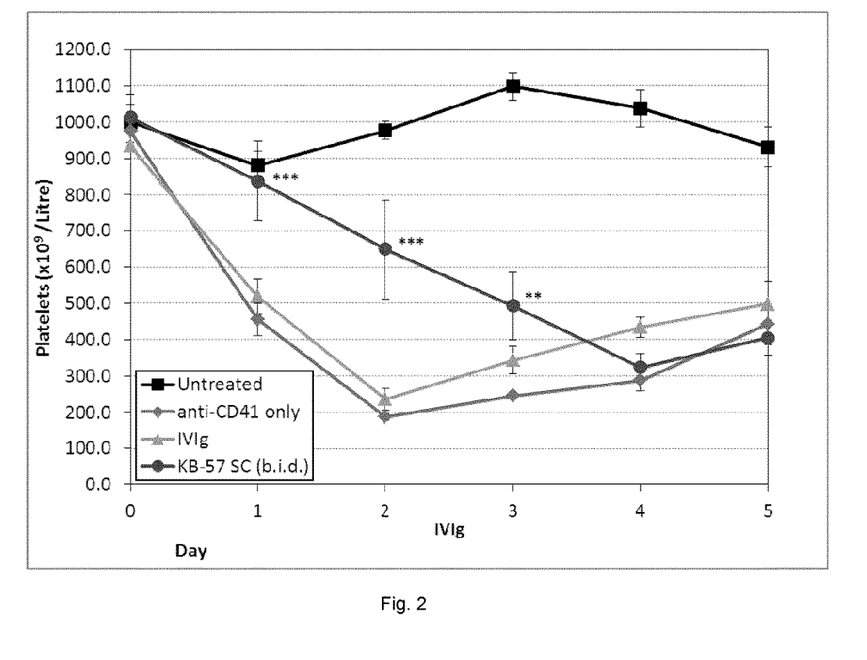
FIG. 2 is showing the efficacy of a compound of this disclosure given subcutaneously at preventing ITP in vivo.

Compound 50 given subcutaneously (SC) is efficacious for the amelioration of ITP in the preventive mouse model of ITP. Mice were treated as above with an anti-platelet antibody (rat anti-mouse CD41 using 1.4 µg constant dose) daily starting at Day 0 to induce ITP. Compound 50 was given SC twice per day (2 sites, 2 mg/ml) starting at Day 0. IVIg (1 g/kg) was given on Day 2 for comparison as this is considered the therapeutic dose of IVIg. Treatment groups: n=5 mice per group; control (untreated): n=3. Statistical significance by one-way ANOVA with Dunnett posthoc test and is indicated:  $p<0.01$; * $p<0.001$.

In another embodiment, the present invention provides a combination comprising a therapeutically effective amount of a compound, as defined herein, and a therapeutically effective amount of at least one or more therapeutic agents useful in the method of the present disclosure including but not limited to corticosteroids, rituximab, intravenous immunoglobulins (IVIG and anti-D), TPO agonists etc. The one or more therapeutic agent can operate through the same molecular mechanism as the compounds defined herein or a molecular mechanism.

In one aspect there is provided a method for the prevention, treatment and/or alleviation of one or more symptoms of an autoimmune or alloimmune disease associated with a type II hypersensitivity reaction comprising administering to a subject in need thereof a therapeutically effective amount of a compound as defined herein.

In one aspect there is provided a method for the prevention, treatment and/or alleviation of one or more autoimmune or alloimmune disease comprising administering to a subject in need thereof a therapeutically effective amount of a compound as defined herein.

In one embodiment, the autoimmune disease is at least one of immune thrombocytopenia, autoimmune haemolytic anemia, Graves' disease, myasthenia gravis, bullous pemphigoid, *pemphigus vulgaris*, rheumatic fever or Goodpasture's syndrome.

In one embodiment, the autoimmune disease is immune thrombocytopenia.

In one embodiment, the autoimmune disease is immune thrombocytopenia and refractory immune thrombocytopenia.

In one embodiment, the alloimmune disease is alloantibody-mediated haemolytic transfusion reaction, disease of the fetus and newborn or pernicious anemia.

In one aspect, there is provided a method of limiting or inhibiting the phagocytosis of a blood cell or a blood fragment wherein the blood cell or blood fragment is coated with autoantibodies or alloantibodies, said method comprising administering to a subject in need thereof a therapeutically effective amount of a compound as defined herein.

In one embodiment, the blood fragment is a platelet.

In one embodiment, the autoantibodies or alloantibodies are IgG antibodies.

In one embodiment, the phagocytic cell is a monocyte, a macrophage, a neutrophil or a combination thereof. In a further embodiment, the phagocytic cell is liver and splenic tissue macrophages.

It will be clear to a person of ordinary skill that the amount of the compound described herein and used in accordance with the disclosure (or if a further additional therapeutic agent is required or desired) can be determined by the attending physician or pharmacist. It will be appreciated that the amount of a compound required will vary not only with the particular compound selected but also with the route of administration, the nature of the condition for which treatment is required and the age and condition of the patient.

It will be understood that the scope of the method of treatment or uses described herein is not particularly limited, but includes in principle any therapeutically useful outcome including preventing, treating or slowing the progression of conditions or diseases defined herein.

The desired dose may conveniently be presented in a single dose or as divided dose administered at appropriate intervals, for example as two, three, four or more doses per day.

Pharmaceutical compositions include, without limitation, those suitable for oral, (including buccal and sub-lingual), transdermal, or parenteral (including intramuscular, subcutaneous and intravenous) administration or in a form suitable for administration by inhalation.

The formulations may, where appropriate, be conveniently presented in discrete dosage units and may be prepared by any of the methods well known in the art of pharmacy. The methods for preparing a pharmaceutical composition can include the steps of bringing into association the compound as defined herein and pharmaceutically acceptable excipient(s) or carrier(s) and then, if necessary, shaping the product into the desired formulation, including applying a coating when desired.

The compounds and combinations as defined herein may formulated for oral administration and conveniently be presented as discrete units such as capsules, cachets or tablets each containing a predetermined amount of the active ingredient; as a powder or granules; as a solution, a suspension or as an emulsion. Tablets and capsules for oral administration may contain conventional excipient(s) or carrier(s) such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds and combinations as defined herein may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile water or saline, before use.

Compositions suitable for topical administration in the mouth include lozenges comprising the active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

For administration by inhalation, the compounds and combinations as defined herein may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

While the invention has been described in connection with specific embodiments thereof, it is understood that it is capable of further modifications and that this application is intended to cover any variation, use, or adaptation of the invention following, in general, the principles of the invention and including such departures from the present disclosure that come within known, or customary practice within the art to which the invention pertains and as may be applied to the essential features hereinbefore set forth.

The invention claimed is:

1. A compound of formula:

or a pharmaceutically acceptable salt thereof; wherein
U is an alkylene residue of 1-4 members wherein one or two non-consecutive carbon atom is optionally independently replaced by O or NR10;
Q is wherein each R1 is independently H, alkyl, amino or halogen;
each R2 is H;
each R3 is independently aryl, -alkyl-aryl, cycloalkyl, or -alkyl-cycloalkyl; and
R4 is hydroxyl, hydroxyalkyl or halogen;
R10 is H or a lower alkyl;
wherein each of the alkyl and aryl is optionally substituted.

2. The compound or a pharmaceutically acceptable salt thereof of claim 1, wherein R1 is H or alkyl.

3. The compound or a pharmaceutically acceptable salt thereof of claim 1, wherein R1 is C1-3 alkyl.

4. The compound or a pharmaceutically acceptable salt thereof of claim 1, wherein R3 is C6-10-aryl, —C1-2alkyl-C6-10aryl, C5-6-cycloalkyl, or —C1-2alkyl-C5-6cycloalkyl.

5. The compound or a pharmaceutically acceptable salt thereof of claim 1, wherein R3 is phenyl, $CH_2$-phenyl; cyclopentyl; cyclohexyl, $CH_2$-cyclopentyl; $CH_2$-cyclohexyl; $CH_2$—COOH or $CH_2CH_2NH_2$.

6. The compound or a pharmaceutically acceptable salt thereof of claim 1, wherein U is an alkylene residue of 1-4 members wherein one carbon atom is optionally independently replaced by O.

7. The compound or a pharmaceutically acceptable salt thereof of claim 1, wherein U is an alkylene residue of 2-3 members, wherein one carbon atom is replaced by O or NR10.

8. The compound or a pharmaceutically acceptable salt thereof of claim 1, wherein U is $CH_2$—$CH_2$, $CH_2$; $CH_2$—O, O—$CH_2$; or $CH_2$—NH—$CH_2$.

9. The compound or a pharmaceutically acceptable salt thereof of claim 1, wherein Q is and R4 is hydroxyl.

10. A pharmaceutical composition comprising a compound as defined in claim 1 or a pharmaceutically acceptable salt thereof; in combination with one or more pharmaceutically acceptable carrier or excipient.

11. A compound of formula:

or a pharmaceutically acceptable salt thereof; wherein
U is $CH_2$—$CH_2$ or $CH_2$;
R1 is independently an alkyl of 1-3 carbon atoms,
R2 is H;
R3 is phenyl, or benzyl; and
R4 is hydroxyl ;
wherein each of the alkyl is optionally substituted.

12. The compound or a pharmaceutically acceptable salt thereof of claim 1, having the formula:

wherein:
U is $CH_2$, $CH_2$—$CH_2$, $CH_2$—O, O—$CH_2$; or $CH_2$—NH—$CH_2$;
each R1 is independently an alkyl of 1-3 carbon atoms;
R2 is H;
R3 is independently C6-10-aryl, —C1-2alkyl-C6-10aryl, C5-6-cycloalkyl, —C1-2alkyl-C5-6cycloalkyl or C1-6 substituted alkyl; and
R4 is hydroxyl;
wherein each of the alkyl and aryl is optionally substituted.

13. A compound having the formula

| Cpd # | Formula |
|---|---|
| 14 | |
| 15 | |
| 18 | |
| 20 | |
| 24 | |

-continued

| Cpd # | Formula |
|---|---|
| 28 | (structure) |
| 32 | (structure) |
| 37 | (structure) |
| 41 | (structure) |
| 47 | (structure) |
| 48 | (structure) |
| 50 | (structure) |
| 53 | (structure) | or a pharmaceutically acceptable salt thereof.

* * * * *

UNITED STATES PATENT AND TRADEMARK OFFICE
CERTIFICATE OF CORRECTION

PATENT NO. : 10,130,609 B2
APPLICATION NO. : 14/775449
DATED : November 20, 2018
INVENTOR(S) : Donald R. Branch and Lakshmi P. Kotra It is certified that error appears in the above-identified patent and that said Letters Patent is hereby corrected as shown below:

In the Claims

Beginning at Column 26, Line 16, delete all claims and replace with the following claims:

1. A compound of formula:

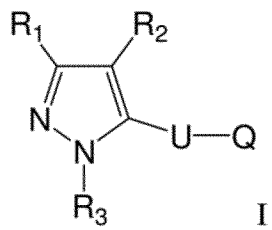

I or a pharmaceutically acceptable salt thereof; wherein
U is an alkylene residue of 1-4 members wherein one or two non-consecutive carbon atom is optionally independently replaced by O or NR10;

Q is 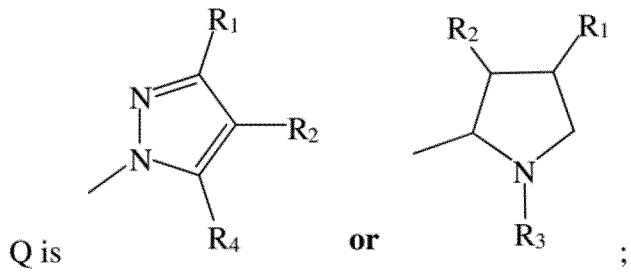 ;

wherein each R1 is independently H, alkyl, amino or halogen;
each R2 is H;
each R3 is independently aryl, -alkyl-aryl, cycloalkyl, or -alkyl-cycloalkyl; and
R4 is hydroxyl, hydroxyalkyl or halogen;
R10 is H or a lower alkyl;
wherein each of the alkyl and aryl is optionally substituted.

Signed and Sealed this
Twenty-fourth Day of November, 2020

Andrei Iancu
*Director of the United States Patent and Trademark Office*

2. The compound or a pharmaceutically acceptable salt thereof of claim 1, wherein R1 is H or alkyl.

3. The compound or a pharmaceutically acceptable salt thereof of claim 1, wherein R1 is C1-3 alkyl.

4. The compound or a pharmaceutically acceptable salt thereof of claim 1, wherein R3 is C6-10-aryl, -C1-2alkyl-C6-10aryl, C5-6-cycloalkyl, or -C1-2alkyl-C5-6cycloalkyl.

5. The compound or a pharmaceutically acceptable salt thereof of claim 1, wherein R3 is phenyl, $CH_2$-phenyl; cyclopentyl; cyclohexyl, $CH_2$-cyclopentyl; $CH_2$-cyclohexyl; $CH_2$-COOH or $CH_2CH_2NH_2$.

6. The compound or a pharmaceutically acceptable salt thereof of claim 1, wherein U is an alkylene residue of 1-4 members wherein one carbon atom is optionally independently replaced by O.

7. The compound or a pharmaceutically acceptable salt thereof of claim 1, wherein U is an alkylene residue of 2-3 members, wherein one carbon atom is replaced by O or NR10.

8. The compound or a pharmaceutically acceptable salt thereof of claim 1, wherein U is $CH_2$-$CH_2$, $CH_2$; $CH_2$-O, O-$CH_2$; or $CH_2$-NH-$CH_2$.

9. The compound or a pharmaceutically acceptable salt thereof of claim 1, wherein Q is

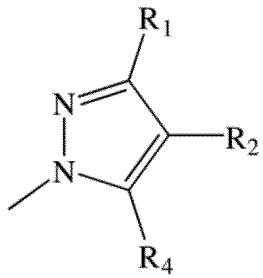

and R4 is hydroxyl.

10. A compound having the formula

| Cpd# | Formula | Cpd# | Formula |
|---|---|---|---|
| 14 | 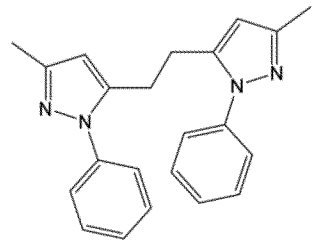 | 37 | 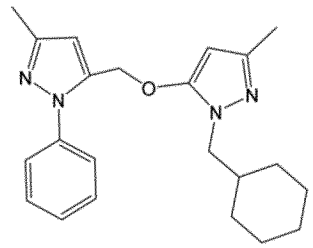 |

15 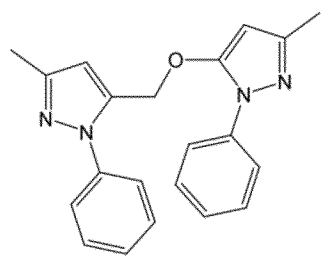 41 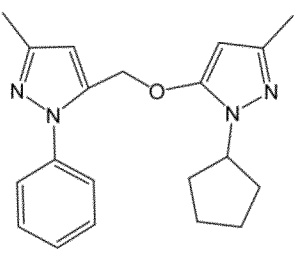
18 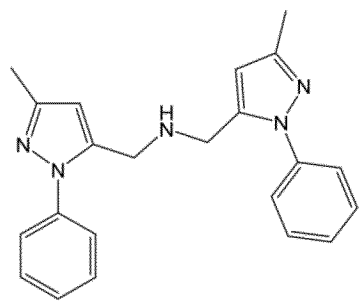 47 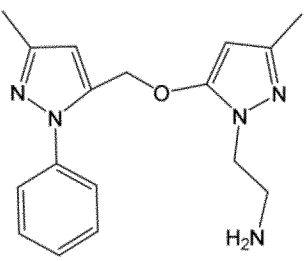
20 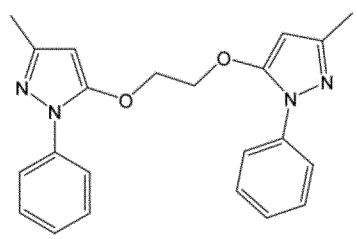 48 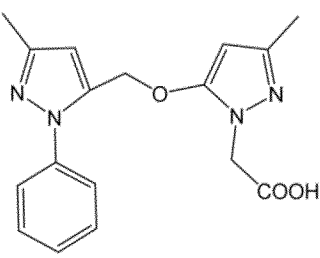
24 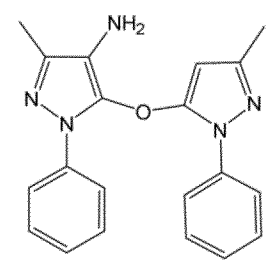 50 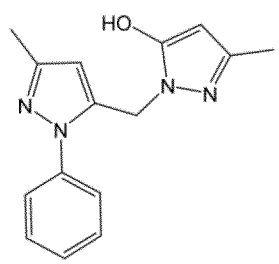
28 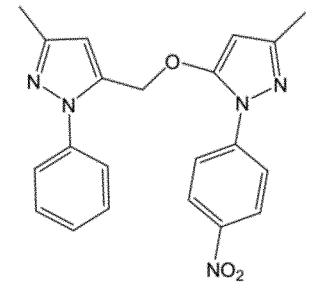 53 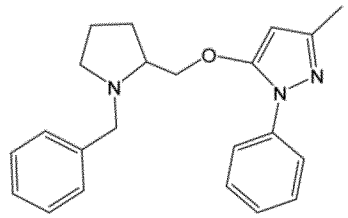

32

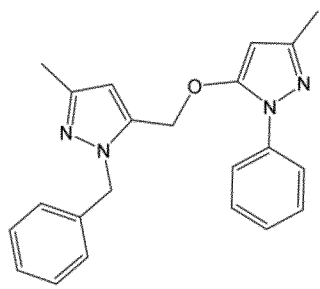

or a pharmaceutically acceptable salt thereof.

11. A compound of formula:

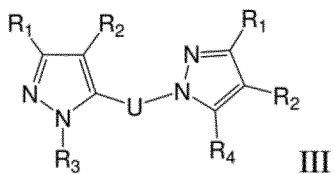

or a pharmaceutically acceptable salt thereof; wherein
U is $CH_2$-$CH_2$ or $CH_2$;
R1 is independently an alkyl of 1-3 carbon atoms,
R2 is H;
R3 is phenyl, or benzyl; and
R4 is hydroxyl;
wherein each of the alkyl is optionally substituted.

12. A pharmaceutical composition comprising a compound as defined in claim 1 or a pharmaceutically acceptable salt thereof; in combination with one or more pharmaceutically acceptable carrier or excipient.

13. The compound or a pharmaceutically acceptable salt thereof of claim 1, having the formula:

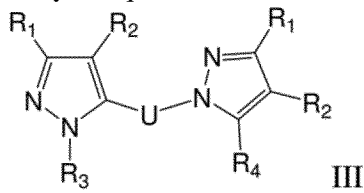

wherein:
U is $CH_2$, $CH_2$-$CH_2$, $CH_2$-O, O-$CH_2$; or $CH_2$-NH-$CH_2$;
each R1 is independently an alkyl of 1-3 carbon atoms;
R2 is H;
R3 is independently C6-10-aryl, -C1-2alkyl-C6-10aryl, C5-6-cycloalkyl, -C1-2alkyl-C5-6cycloalkyl or C1-6 substituted alkyl; and
R4 is hydroxyl;
wherein each of the alkyl and aryl is optionally substituted.